United States Patent
Chien (10) Patent No.: US 11,769,252 B2
(45) Date of Patent: Sep. 26, 2023

(54) SYSTEMS AND METHODS FOR INTRA-PROCEDURE IMAGE-BASED FLOW QUANTIFICATION

(71) Applicant: The Regents of the University of California, Oakland, CA (US)

(72) Inventor: Aichi Chien, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 321 days.

(21) Appl. No.: 17/263,843

(22) PCT Filed: Jul. 29, 2019

(86) PCT No.: PCT/US2019/043907
§ 371 (c)(1),
(2) Date: Jan. 27, 2021

(87) PCT Pub. No.: WO2020/028246
PCT Pub. Date: Feb. 6, 2020

(65) Prior Publication Data
US 2021/0312619 A1    Oct. 7, 2021

Related U.S. Application Data

(60) Provisional application No. 62/711,756, filed on Jul. 30, 2018.

(51) Int. Cl.
*G06T 7/00* (2017.01)
*A61B 6/00* (2006.01)
(Continued)

(52) U.S. Cl.
CPC ............ *G06T 7/0012* (2013.01); *A61B 5/026* (2013.01); *A61B 5/055* (2013.01); *A61B 6/481* (2013.01);
(Continued)

(58) Field of Classification Search
CPC ......... G06T 7/0012; G06T 2207/10081; G06T 2207/10088; G06T 2207/10116;
(Continued)

(56) References Cited

U.S. PATENT DOCUMENTS

| 2005/0065432 A1 | 3/2005 | Kimura |
| 2008/0020362 A1 | 1/2008 | Cotin |

(Continued)

FOREIGN PATENT DOCUMENTS

| WO | 02/056666 A2 | 7/2002 |
| WO | 2005/054898 A1 | 6/2005 |

OTHER PUBLICATIONS

S. Eren et al., Plastic and Reconstructive Surgery, vol. 96, No. 7, Dec. 1995, pp. 1636-1649.

(Continued)

*Primary Examiner* — Siamak Harandi
(74) *Attorney, Agent, or Firm* — Quarles & Brady LLP (57) ABSTRACT

A system and method is provided for assessing efficacy of placement of a vascular implant medical device that has been implanted in a subject. The method includes accessing, with a computer system, image data acquired from a subject using a medical imaging system. The image data include at least one image of the vascular implant device implanted within a vascular structure of the subject after the subject has received an injection of a contrast agent at a contrast injection site. The method also includes determining, from the image data, a region of interest (ROI) that includes the vascular structure and is downstream of the contrast injection site and developing a contrast model from the image data. The method further includes, using the contrast model, determining a flow time constant and, using the flow time constant, assessing an efficacy of the vascular implant device implanted in the vascular structure.

24 Claims, 9 Drawing Sheets

(51) Int. Cl.
    *A61B 5/026* (2006.01)
    *A61B 5/055* (2006.01)
(52) U.S. Cl.
    CPC .... *A61B 6/504* (2013.01); *G06T 2207/10081* (2013.01); *G06T 2207/10088* (2013.01); *G06T 2207/10116* (2013.01); *G06T 2207/30104* (2013.01)
(58) Field of Classification Search
    CPC .......... G06T 2207/30104; A61B 5/026; A61B 5/055; A61B 6/481; A61B 6/504; A61B 5/4851; A61F 2/2427
    See application file for complete search history.

(56) References Cited

U.S. PATENT DOCUMENTS

| | | | |
|---|---|---|---|
| 2008/0294035 A1* | 11/2008 | Zwick | A61B 5/055 382/128 |
| 2011/0235885 A1 | 9/2011 | Rauch | |
| 2011/0274333 A1 | 11/2011 | Prevrhal | |
| 2012/0253190 A1 | 10/2012 | Gauthier | |
| 2012/0323127 A1 | 12/2012 | Boyden | |
| 2015/0320357 A1 | 11/2015 | Karaguntla | |

OTHER PUBLICATIONS

Endres, J., et al., A workflow for patient-individualized virtual angiogram generation based on CFD simulation. Comput Math Methods Med, 2012. 2012: p. 306765.

Fanelli, F., et al., Management of Refractory Hepatic Encephalopathy After Insertion of TIPS: Long-Term Results of Shunt Reduction With Hourglass-Shaped Balloon-Expandable Stent-Graft. American Journal of Roentgenology, 2009. 193: p. 1696-1702.

Fidelman, N., et al., The Transjugular Intrahepatic Portosystemic Shunt: An Update. American Journal of Roentgenology, 2012. 199: p. 746-755.

International Searching Authority. International Search Report and Written Opinion for application PCT/US2019/043907, dated Oct. 17, 2019. 7 pages.

Klasen-Sansone, J., et al., TIPS geometry influences patency. Zeitschrift Fur Gastroenterologie, 2015. 53: p. 28-32.

Nardelli, S., et al., Cognitive Impairment Predicts the Occurrence of Hepatic Encephalopathy After Transjugular Intrahepatic Portosystemic Shunt. The American Journal of Gastroenterology, 2016. 111: p. 523-528.

Preibsch, H., et al., Impact of transjugular intrahepatic portosystemic shunt implantation on liver perfusion measured by volume perfusion CT. Acta Radiologica, 2017: p. 284185116685922.

Silva-Junior, G., et al., Timing Affects Measurement of Portal Pressure Gradient After Placement of Transjugular Intrahepatic Portosystemic Shunts in Patients With Portal Hypertension. Gastroenterology, 2017.

Wakhloo, A.K., et al., A novel approach to flow quantification in brain arteriovenous malformations prior to enbucrilate embolization: use of insoluble contrast (Ethiodol droplet) angiography. J Neurosurg, 1998. 89(3): p. 395-404.

\* cited by examiner

SYSTEMS AND METHODS FOR INTRA-PROCEDURE IMAGE-BASED FLOW QUANTIFICATION

CROSS-REFERENCE TO RELATED APPLICATIONS

The present application represents the national stage entry of International Application PCT/US2019/043907, filed Jul. 29, 2019, which claims the benefit of U.S. Provisional Patent Application Ser. No. 62/711,756 filed on Jul. 30, 2018 and entitled "Systems and Methods for Intra-Procedure Image-Based Flow Quantification."

STATEMENT REGARDING FEDERALLY SPONSORED RESEARCH

N/A

BACKGROUND

Evaluation of flow of biological fluids, for example blood or cerebrospinal fluid can provide useful information for clinical diagnosis and treatment planning. If determined during a medical procedure, this information can help clinical management and provide immediate evaluation of the procedure performed and help direct modifications of the procedure if needed. To date, quantitative evaluation of disease and medical procedures based on medical images has rarely been performed intra-procedurally.

Transjugular intrahepatic portosystemic shunt (TIPS) creation is an effective method for reducing the portosystemic gradient (PSG) in the treatment of the complications of portal hypertension. In cases in which complications reoccur, TIPS angioplasty may be required, whereas in cases in which refractory hepatic encephalopathy (HE) develops, a reduction in the shunt may be needed to reduce flow. Recent studies suggest that catheter based PSG measurements during a procedure may not be consistent with those made 1 day or 1 month later and may correlate poorly with other methods of measuring pressure or flow.

Although catheter-based measurement is one way of determining whether TIPS creation has sufficiently reduced PSG, its predictive value for future complications or TIPS revision is less clear. Recent research indicates a correlation between TIPS geometry (angle and location) and shunt patency. Thus, additional methods of quantitatively assessing TIPS creation may increase treatment success and reduce the need for revision.

SUMMARY OF THE DISCLOSURE

The present disclosure addresses the aforementioned drawbacks by providing a system and method for image based flow quantification to predict a need for adjustment, modification, or revision of an implanted medical device. Clinical images may be used to directly extract quantitative data, such as flow parameters and flow measurements, and the like. In one configuration, the implanted device is a Transjugular intrahepatic portosystemic shunt (TIPS) and the image based flow quantification includes assessing portal vein blood flow to predict a subsequent need for TIPS revision.

In one configuration, a method is provided for assessing efficacy of placement of a vascular implant medical device that has been implanted in a subject. The method includes accessing, with a computer system, image data acquired from a subject using a medical imaging system. The image data include at least one image of the vascular implant device implanted within a vascular structure of the subject after the subject has received an injection of a contrast agent at a contrast injection site. The method further includes determining, from the image data, a region of interest (ROI) that includes the vascular structure and is downstream of the contrast injection site. The method also includes developing a contrast model from the image data and, using the contrast model, determining a flow time constant. The method includes, using the flow time constant, assessing an efficacy of the vascular implant device implanted in the vascular structure.

In one configuration, a system is provided for assessing efficacy of a vascular implant device that has been implanted in a particular position in a subject. The system includes a computer system configured to access image data acquired from a subject using a medical imaging system. The image data includes at least one image of the vascular implant device implanted within the subject at a time after the subject has received an injection of a contrast agent at a contrast injection site. The computer system is further programmed to determine, from the image data, a region of interest (ROI) downstream of the contrast injection site and develop a contrast model from the image data. The computer system is further programmed to use the contrast model to calculate a flow time constant and generate a report indicating an efficacy of the vascular implant device in the particular position in the subject using the flow time constant. The system further includes a display configured to display the report.

In one configuration, a method is provided for supporting a clinical decision by characterizing the flow of a fluid within a subject. The method includes accessing, with a computer system, image data acquired from a subject using a medical imaging system, wherein the image data include at least one image of a vasculature of the subject. The method also includes determining, from the image data, a region of interest (ROI) downstream of a source of the fluid in the subject and extracting, using the image data, voxel intensity values for the ROI over time. The method further includes fitting the voxel intensity values to a contrast model, calculating a flow time constant using the contrast model, and generating a report indicating efficacy of flow through the vasculature.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Image based flow quantification may be used for diagnosis, evaluation of health conditions or disease progression, as well as procedure planning, and decision making. Image based flow quantification may also be used to predict a need for adjustment, modification, or revision of an implanted medical device. Applications of the present disclosure include, but are not limited to, evaluation of the need for flow improvement using cardiac stenting, the improvement of flow after cardiac stenting, flow following implantation of a flow diverting stent, and flow improvement after Transjugular intrahepatic portosystemic shunt (TIPS) creation. Other utilizations could include peripheral vascular disease clinical evaluation, renal stenting, ischemic stroke stenting and thrombectomy.

In some configurations of the image based flow quantification, the flow may be of a contrast agent. Processes where a contrast agent or other labeled media is introduced in a single location and is gradually cleared might be quantified in the same manner as the flow of a biological fluid. In some configurations, the flow which is quantified could be of any biological fluid, such as blood, CSF, air, and the like, or may be a combination of biological fluids.

In some configurations, image based flow quantification might be performed intra-procedurally, such as to guide adjustment of a device during an implantation procedure. In some configurations, the image based flow quantification might be based on images routinely acquired, i.e. make additional use of medical images routinely acquired as part of a procedure or evaluation, instead of requiring an additional image acquisition for the specific purpose of flow quantification.

Any imaging modality may be used with the present disclosure and the disclosure is not restricted to a particular imaging modality. Many different modalities are compatible with flow quantification, such as fluoroscopy, x-ray imaging, digital subtraction angiography, magnetic resonance, computed tomography, nuclear medicine imaging, and ultrasound, among others. In some configurations, a combination of imaging modalities may be used. Any contrast agent or combination of contrast agents may be used with the present disclosure and the disclosure is not restricted to a particular contrast agent. In some configurations, a contrast agent may not be required where labeling is provided by other methods, such as magnetic resonance imaging approaches which tag a volume with a special pulse sequence. In some configurations, labeling might be of fluid or of tissue adjacent to a region of interest through which a fluid will flow.

In some configurations, image based flow quantification may evaluate a change in a particular region of interest over the course of a series of medical images which corresponds to flow of a biological fluid. This change may be based on the image intensity in that region, signals existing in the fluid itself, or a differential value between the fluid and the surrounding tissue or objects.

Figure 1A:
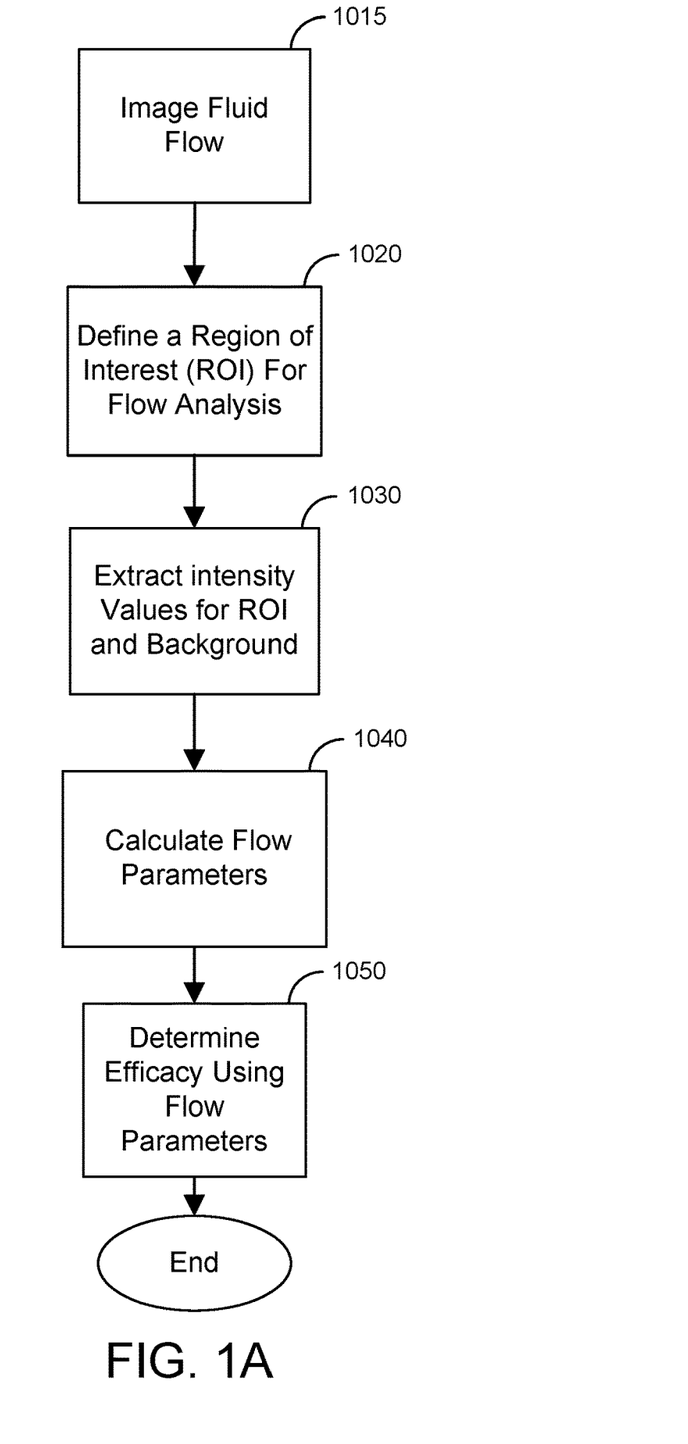
FIG. 1A is a flowchart of non-limiting example steps for one configuration to implement a method of the present disclosure for a fluid.

Referring to FIG. 1A, a flowchart depicting non-limiting example steps for implementing one configuration of the present disclosure is shown with the process starting with imaging a fluid, such as a biological fluid, at step 1015. A region of interest (ROI) is defined at step 1020 and may be selected to be downstream from a fluid source, such as a contrast injection being administered to a subject, or an organ, and the like. The intensity values for the pixels or voxels of the ROI are extracted at step 1030. The background signal may be selected as a suitable location away from the ROI and this background signal may also be subtracted from the intensity values at step 1030. The intensity values are used with a contrast model to determine flow parameters at step 1040. An efficacy of the device as currently deployed may be determined at step 1050 based upon the flow parameters. If the efficacy does not meet a threshold, for example, a treatment recommendation may be made, which may assist a clinical decision, such as a need for revision, or assessing the risk or a probability for a revision, adjustment, or modification of an implant, and the like.

Figure 1B:
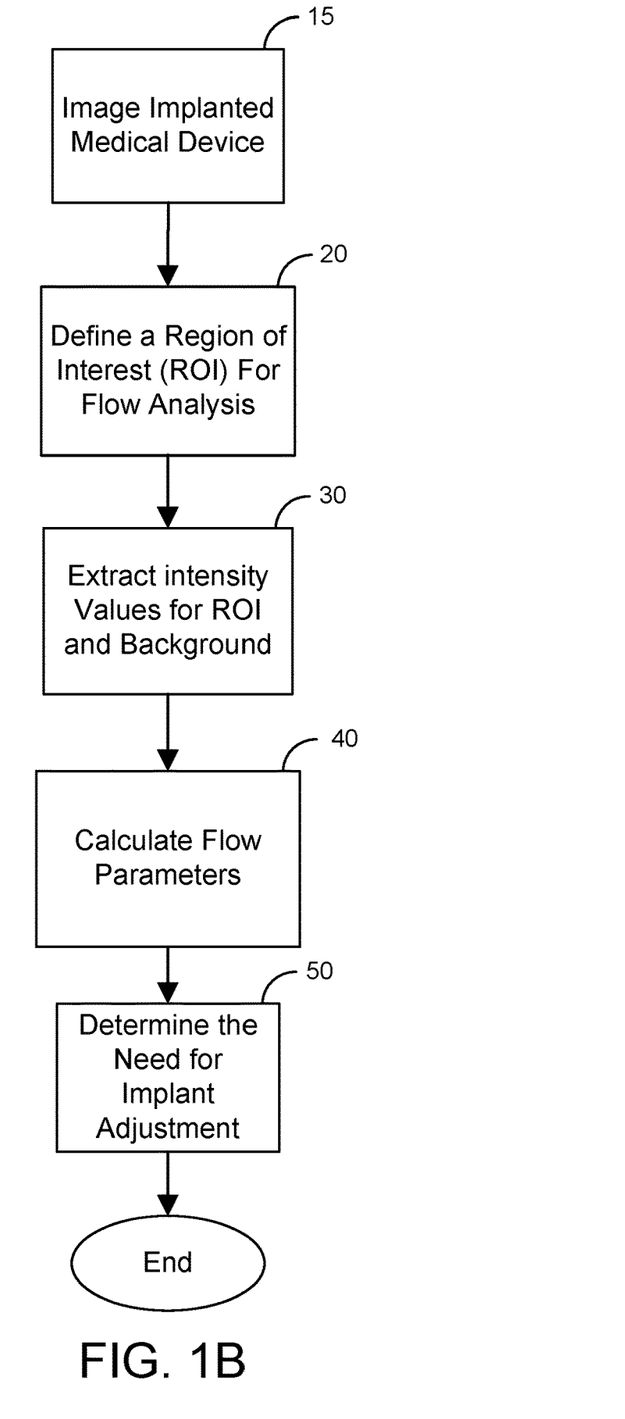
FIG. 1B is a flowchart of non-limiting example steps for one configuration to implement a method of the present disclosure for an implanted medical device.

Referring to FIG. 1B, a flowchart depicting non-limiting example steps for implementing one configuration of the present disclosure is shown with the process starting with imaging an implanted medical device at step 15. A region of interest (ROI) is defined at step 20 and may be selected to be downstream from a contrast injection being administered to a subject. The intensity values for the pixels or voxels of the ROI are extracted at step 30. The background signal may be selected as a suitable location away from the ROI and this background signal may also be subtracted from the intensity values at step 30. The intensity values are used with the contrast model, and flow parameters can be calculated at step 40. The risk or the probability of a need for revision, adjustment, or modification of the implant can be determined at step 50.

A contrast model for may be based upon multiple constants, not just a curve of contrast intensity over time. In one non-limiting example, the contrast model may include 3 primary constraints: $Q_\tau$, $c_{max}$, and $t_0$.

$$c(t) = \begin{cases} 0 & t < t_a \\ c_{max} - e^{(t_0 - Q_\tau t)} & t_a \leq t < t_b \\ e^{(t_0 - Q_\tau t)} & t_b < t \end{cases}$$

where $Q_\tau$ is the flow time constant. When flow is faster, the contrast increases faster in the ROI and the $Q_\tau$ is larger. The variable c represents contrast intensity; t, time; and ta and $t_b$ are the bolus injection start and stop times, respectively. The term $c_{max}$ may correspond to the maximum contrast intensity during the image series, and $t_0$ is a factor to account for delay between the start of imaging and contrast increase.

From an image series documenting flow after a procedure, such as a TIPS creation, the intensity values for the ROI and a background region for each frame may be extracted. These values may be used to fit an enhancement curve, such as created using the contrast model described above. The enhancement curve may include background subtracted data. In one configuration, the enhancement curve may be fit using a least squares method to calculate the flow parameters for each case, such as $Q_\tau$, $c_{max}$, and $t_0$. Lower values of the flow time constant $Q_\tau$ may indicate a slower flow rate. Flow rate may be lower in cases that require no revision and may be higher in the cases that eventually require a shunt reduction.

Figure 2:
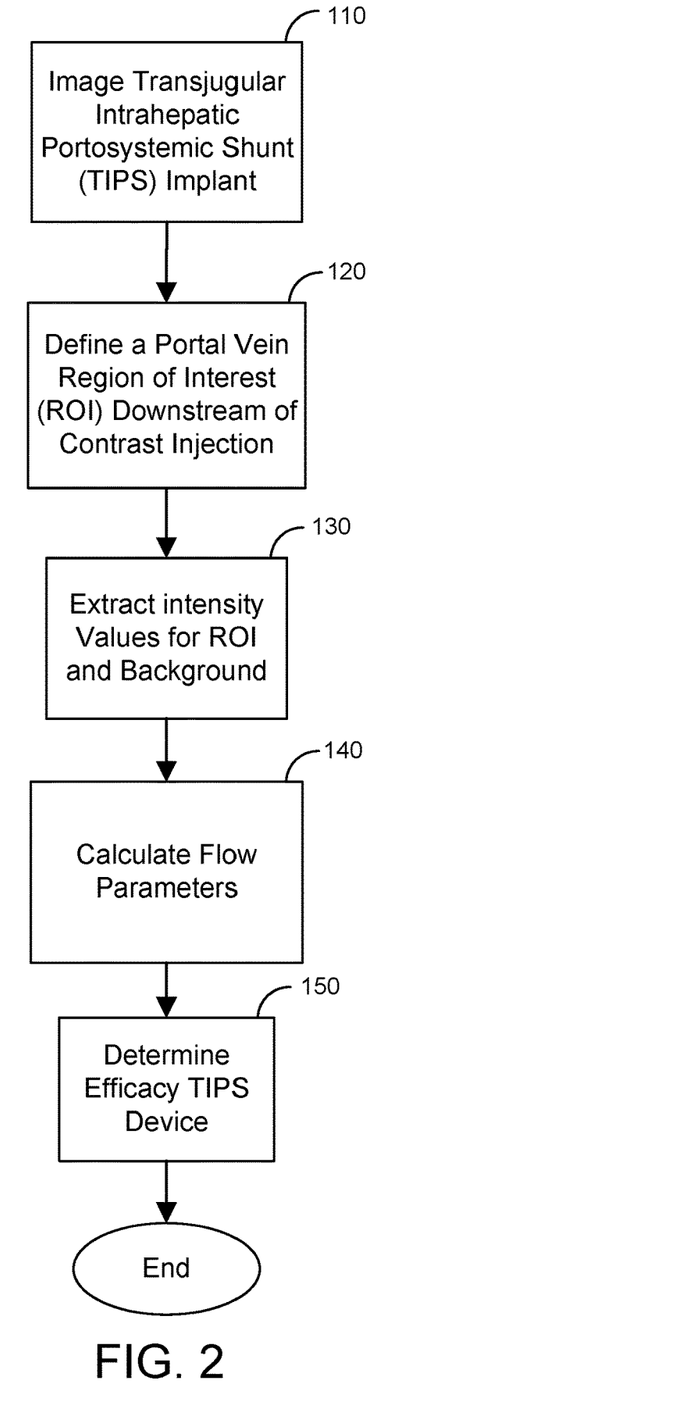
FIG. 2 is a flowchart of non-limiting example steps for one configuration to implement a method of the present disclosure for a TIPS implant.

Referring to FIG. 2, a flowchart depicting non-limiting example steps for implementing one configuration of the present disclosure is shown with the process starting with imaging a TIPS implant at step 110. A region of interest (ROI) is defined at step 120 and may be selected to be downstream from a contrast injection being administered to a subject. In some configurations, the relative location of the contrast injection and the ROI may be on opposing sides of the implant, such that the pixel or voxel ROI values may be indicative of flow across or through the implant. The intensity values for the pixels or voxels of the ROI are extracted at step 130. The background signal may be selected as a suitable location away from the ROI and this background signal may also be subtracted from the intensity values at step 130. The intensity values used with a portal vein enhancement model to determine flow parameters at step 140. The efficacy of the current deployment of the TIPS device is determined at step 150. As will be described, adjustments recommendations or iterative reassessments using alternative and/or potential deployments can be assessed thereafter.

Figure 3:
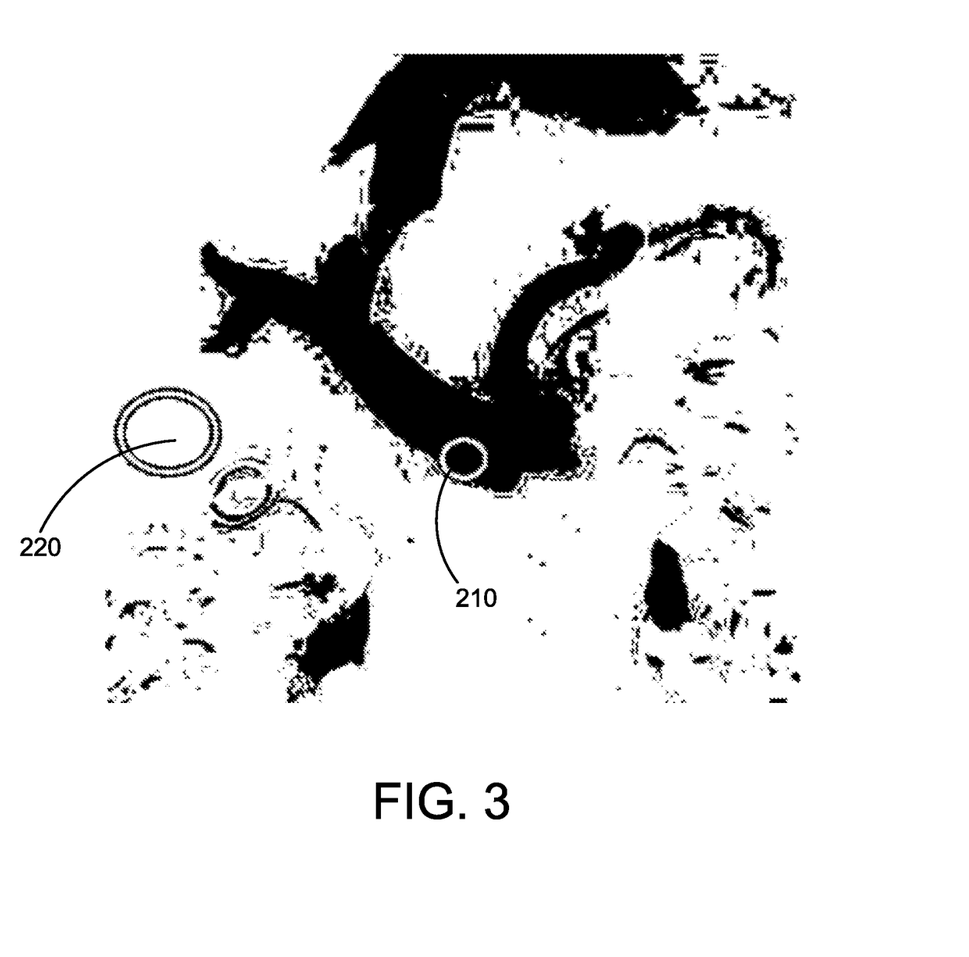
FIG. 3 is a non-limiting example digital subtraction angiography image obtained immediately after transjugular intrahepatic portosystemic shunt creation showing an example ROI and background selection.

Referring to FIG. 3, a non-limiting example contrast-enhanced digital subtraction angiography image obtained immediately after transjugular intrahepatic portosystemic shunt (TIPS) creation is shown. An ROI in the portal vein 210, which may be selected by a user or automatically determined by a computer routine is shown. The background region 220 is also shown and is selected for background subtraction from the intensity values from portal vein ROI 210.

Figure 4:
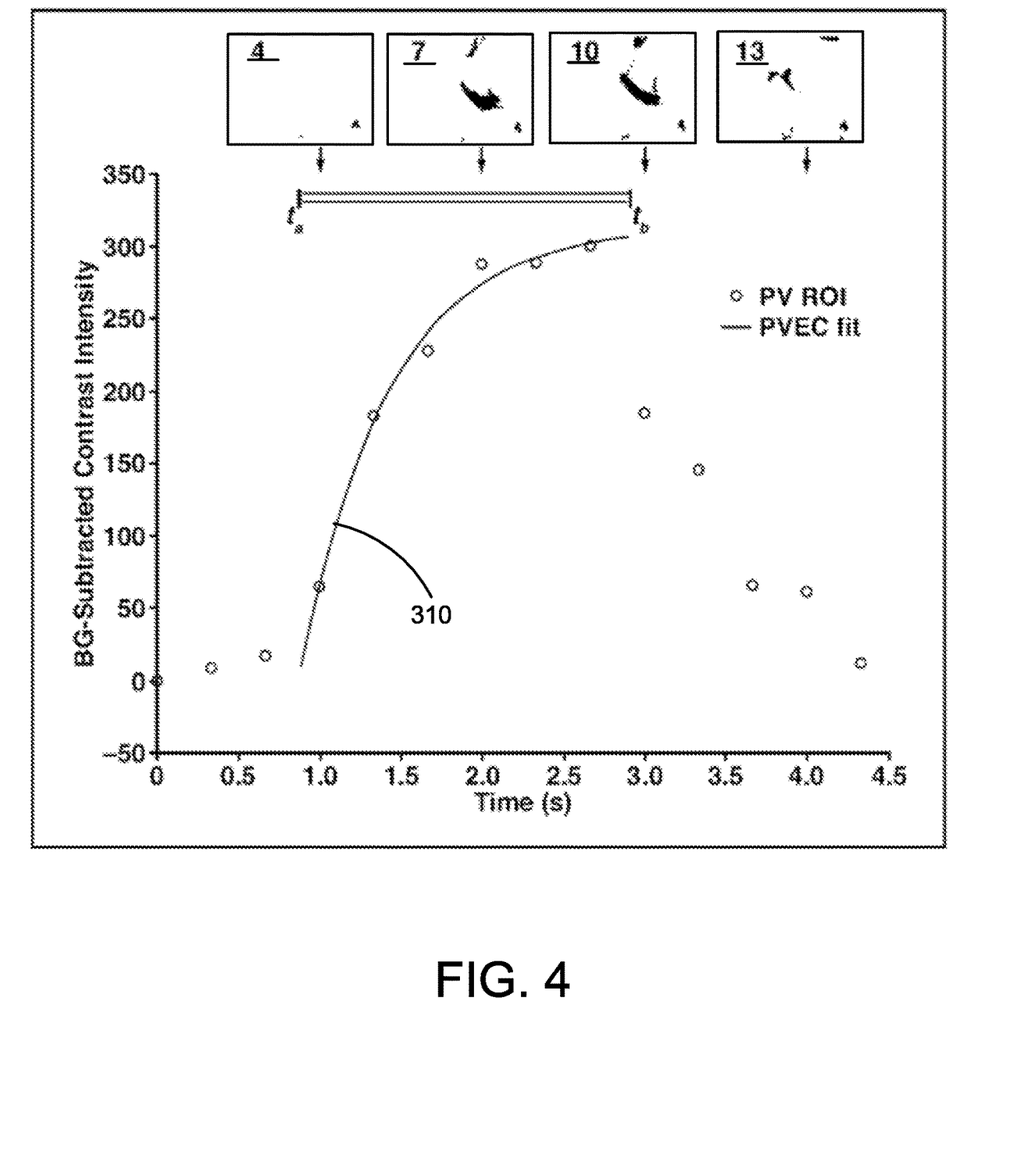
FIG. 4 is a graph of a non-limiting example enhancement curve used in some configurations of the present disclosure.

Referring to FIG. 4, a non-limiting example graph is shown that illustrates how a portal vein enhancement curve (PVEC) model 310 may be used to quantify portal vein flow. Background (BG)-subtracted contrast intensity at the portal vein (PV) ROI was fit to model (i.e., PVEC fit). Labeled images 4, 7, 10, and 13 correspond to time points indicated with arrows. Approximate duration of contrast injection is indicated with gray bar at the top of the graph (from $t_a$ to $t_b$, where $t_a$ and $t_b$ are the bolus injection start and stop times, respectively).

In one configuration, an image-based analysis calculates portal vein flow after TIPS creation. To quantify portal vein flow, a region immediately downstream from the injection site for the contrast agent may be identified within the portal vein as an ROI. The PVEC model may be generated on the basis of contrast agent inflow with the characteristics of a bolus injection. In some configurations where the contrast agent is administered constantly using machine control, the increase in contrast intensity in the portal vein may be analogous to the increase in the charge of a capacitor in a resistor capacitor (RC) circuit, whereby the contrast increases rapidly at first and then asymptotically approaches a steady-state value until the injection ends. A non-limiting example of this behavior may be seen in PVEC model 310 in FIG. 4.

A PVEC model may be based upon multiple constraints. In one non-limiting example, the PVEC model may balance three constants, such as $Q_\tau$, $c_{max}$, and $t_0$.

$$c(t) = \begin{cases} 0 & t < t_a \\ c_{max} - e^{(t_0 - Q_\tau t)} & t_a \leq t < t_b \\ e^{(t_0 - Q_\tau t)} & t_b < t \end{cases}$$

where $Q_\tau$ is the portal vein flow time constant. $Q_\tau$ is defined in an inverse manner as the RC time constant tau ($\tau$): When portal vein flow is faster, the contrast increases faster in the ROI and the $Q_\tau$ is larger. The variable c represents contrast intensity; t, time; and ta and $t_b$ are the bolus injection start and stop times, respectively. The term $c_{max}$ may correspond to the maximum contrast intensity during the image series, and $t_0$ is a factor to account for delay between the start of imaging and contrast increase.

From the image series documenting flow after TIPS creation, the intensity values for the ROI and a background region for each frame may be extracted. These values may be used to fit a portal vein enhancement curve generated from the model, such as that depicted in FIG. 4. In one configuration, the portal vein enhancement curve may be fit using a least squares method to calculate the flow parameters for each case, such as $Q_\tau$, $c_{max}$, and $t_0$. Lower values of the portal vein flow time constant $Q_\tau$ may indicate a slower portal vein flow rate. Portal vein blood flow rate may be lower in cases that require either no revision or TIPS angioplasty and may be higher in the cases that eventually require TIPS reduction.

In some configurations, flow parameters provided by the portal vein enhancement curve method may not be calibrated in terms of velocity or volumetric flow. Ultrasound flow measurements may be made in tandem with digital subtraction angiography (DSA) images to create any necessary calibration. In some configurations, improved image processing may also be employed to allow the portal vein enhancement curve method to be successfully applied to more image series.

In some configurations, the present disclosure may provide a new manner to quantitatively interpret standard DSA series. The portal vein enhancement curve method may assess blood flow during TIPS creation, which may be useful to reduce the need for TIPS revision or to guide interventionalists who are learning the procedure or encounter these cases with less regularity.

Example Validation Study

In a non-limiting example validation study, 88 consecutive patients who underwent TIPS creation were identified between January 2014 and December 2015. Across these cases, a standardized machine-controlled contrast injection of iohexol (Omnipaque 350, GE Healthcare) at 10 mL/s for 2 seconds through a 5-French marker pigtail catheter with 10 sideports (Cook Medical) was used. All patients received polytetrafluoroethylene-covered stents (Viatorr, W. L. Gore & Associates).

Final TIPS diameter was determined on the basis of a target PSG between 4 and 10 mm Hg, taking the initial pressure gradient and risk of HE into account. In most cases, the TIPS was first dilated to 8 mm and was then dilated further to 10 mm if the PSG remained greater than 12 mm Hg.

Electronic Medical Record (EMR) review was the primary source for information about patients and TIPS revision. Archived images for each TIPS procedure were collected and anonymized from our hospital's PACS. Images were acquired using an x-ray system (Allura Xper, Philips Healthcare) at 2, 3, or 6 frames-per-second (FPS). Cases without image series documenting flow immediately after TIPS creation were excluded (five cases). An additional 13 cases were excluded because of poor fit during the flow analysis (adjusted r2<0.9). Poor fit was generally an indication of poor image quality, such as excessive movement during image acquisition, poor contrast, or insufficient frame rate to reconstruct contrast inflow. A total of 70 cases were included in the statistical analyses.

Table 1 depicts the statistics for the TIPS cases of the non-limiting example separated into three groups: cases with no revision, those in which TIPS angioplasty was performed (either with or without additional stenting), and those in which a TIPS reduction was performed. The portal vein flow time constant, $Q_\tau$, was significantly different between groups as determined by one-way ANOVA (p=0.002). A Tukey posthoc test revealed that the difference between $Q_\tau$ was significantly lower in the no revision group (mean±SD, 2.0±0.6; p=0.005) and TIPS angioplasty group (1.7±0.6, p=0.002) than in the TIPS reduction group (2.9±1.1). The difference between the no revision and angioplasty groups was not statistically significant (p=0.41). Lower values of the portal vein flow time constant $Q_\tau$ indicate a slower portal vein flow rate, and FIG. 5 indicates that at the end of the TIPS procedure, the portal vein blood flow rate was lower in the cases that required either no revision or TIPS angioplasty and was higher in the cases that eventually required TIPS reduction. The diagnosis of HE after TIPS was also statistically significant between groups as determined by the chi-square test (p=0.008) (Table 1). Although the analysis did not consider the severity of HE, some level of HE was present in all cases for which TIPS reduction was performed. FIG. 6 presents ROC curves for $Q_\tau$ and pressure measurements made after TIPS creation versus after TIPS reduction. The AUC of $Q\tau$ (AUC=0.76) was greater than the pressure measurements.

TABLE 1

| Characteristic | No Revision (n = 55) | TIPS Angioplasty (n = 9) | TIPS Reduction (n = 6) | Significance (p) |
|---|---|---|---|---|
| Age (y), mean ± SD | 57.0 ± 11.0 | 60.0 ± 6.7 | 44.9 ± 26.8 | 0.09 |
| Sex no. of patients | | | | 0.90 |
| Male | 33 | 6 | 4 | |
| Female | 22 | 3 | 2 | 0.71 |
| Cirrhosis no. of patients | | | | |
| Alcoholic | 20 | 3 | 2 | 0.88 |
| Hepatitis | 14 | 3 | 1 | 0.93 |
| NASH | 16 | 2 | 2 | 0.83 |
| Cryptogenic | 5 | 0 | 1 | 0.55 |
| MELD score, mean ± SD | 15.4 ± 7.6 | 16.5 ± 5.6 | 14.5 ± 3.7 | 0.47 |
| BMI, mean ± SD | 27.8 ± 8.3 | 26.9 ± 4.4 | 26.9 ± 5 2 | 0.55 |
| Portal pressure before TIPS (mm Hg), mean ± SD | 26.3 ± 6.2 | 25.4 ± 8.3 | 27.5 ± 3.5 | 0.70 |
| PSG before TIPS, mean ± SD | 17.4 ± 5.4 | 16.3 ± 9.0 | 19.8 ± 7.4 | 0.14 |
| Portal pressure after TIPS (mm Hg), mean ± SD | 19.6 ± 5.7 | 22.3 ± 6.0 | 20.5 ± 6.0 | 0.002 |
| PSG after TIPS, mean ± SD | 6.3 ± 2.5 | 7.0 ± 3.4 | 7.3 ± 3.4 | 0.74 |
| ΔPSG (reduction), mean ± SD | 11.1 ± 5.0 | 10.1 ± 7.1 | 12.5 ± 4.9 | 0.40 |
| TIPS diameter (xx) | 8.1 ± 0.9 | 7.0 ± 1.4 | 9.0 ± 1.4 | |
| $Q_T^a$, mean ± SD | 2.0 ± 0.6 | 1.7 ± 0.6 | 2.9 ± 1.1 | |
| $C_{max}^b$, mean ± SD | 294 ± 118 | 328 ± 169 | 294 ± 92 | |
| $t_0^c$, mean ± SD | 5.9 ± 0.5 | 5.9 ± 0.7 | 6.2 ± 0.6 | |
| Emergent TIPS placement, no. of patients | | | | 0.46 |
| Yes | 47 | 0 | 1 | |
| No | 8 | 9 | 5 | |
| Variceal bleed, no. of patients | | | | 0.86 |
| Yes | 18 | 2 | 1 | |
| No | 37 | 7 | 5 | |
| Refractory ascites, no. of patients | | | | 0.72 |
| Yes | 37 | 6 | 5 | |
| No | 18 | 3 | 1 | |
| Hepatic hydrothorax, no. of patients | | | | 0.65 |
| Yes | 3 | 0 | 0 | |
| No | 52 | 9 | 6 | |
| Thrombosed portal vein, no. of patients | | | | 0.71 |
| Yes | 4 | 1 | 0 | |
| No | 51 | 8 | 6 | |
| HE before TIPS, no. of patients | | | | 0.25 |
| Yes | 13 | 0 | 1 | |
| No | 42 | 9 | 5 | |

TABLE 1-continued

| Characteristic | No Revision (n = 55) | TIPS Angioplasty (n = 9) | TIPS Reduction (n = 6) | Significance (p) |
|---|---|---|---|---|
| HE after TIPS, no. of patients | | | | 0.008 |
| Yes | 19 | 4 | 6 | |
| No | 36 | 5 | 0 | |
| 12-Month survival, no. of patients | | | | 0.36 |
| Yes | 42 | 7 | 3 | |
| No | 13 | 2 | 3 | |

Figure 5:
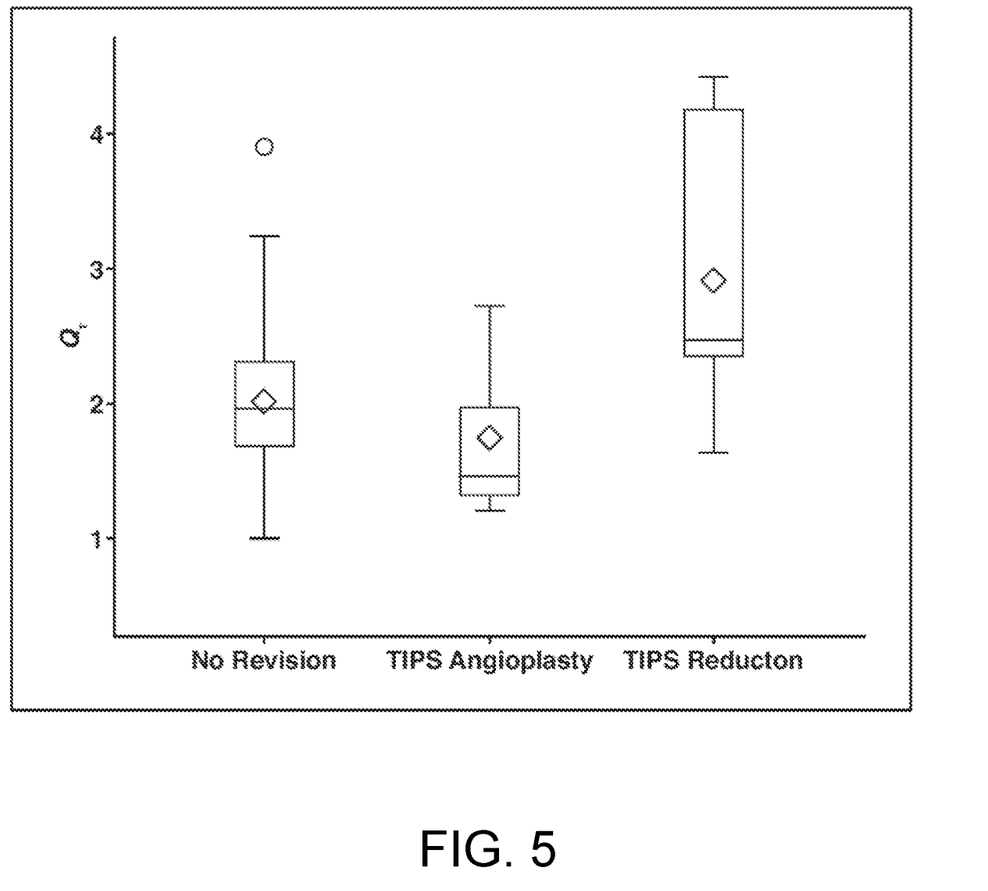
FIG. 5 is a boxplot of non-limiting example portal vein flow time constants resulting from the use of some configurations of the present disclosure.
Figure 6:
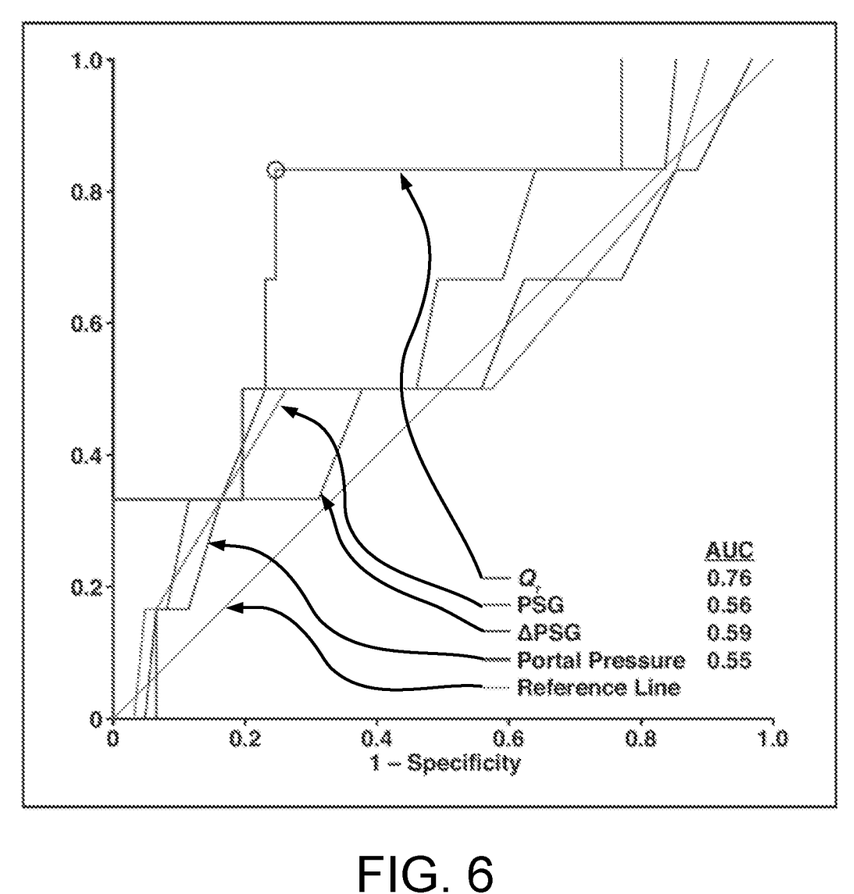
FIG. 6 shows non-limiting example ROC curves for the data of FIG. 5.

Referring to FIG. 5, ANOVA was used for statistical analysis of the non-limiting example data between cases grouped by 12-month revision (no revision, TIPS angioplasty, TIPS reduction). A boxplot (Tukey) of portal vein flow time constant, $Q_\tau$, separated by revision is shown. Diamonds indicate means, and circle indicates outlier (g>1.5). $Q_\tau$ was significantly higher in transjugular intrahepatic portosystemic shunt (TIPS) reduction group (p=0.002), but $Q_\tau$ for no revision group was not significantly different from $Q_\tau$ of TIPS angioplasty group.

Referring to FIG. 6, ROC curves of the non-limiting example data for portal vein flow time constant, $Q_\tau$, portosystemic gradient (PSG) measures, and portal pressure measures made after transjugular intrahepatic portosystemic shunt (TIPS) creation versus after TIPS reduction are shown. Circled point on $Q_\tau$ line is $Q_\tau$ value of 2.3, which had sensitivity of 0.83 and specificity of 0.75.

Figure 7A:
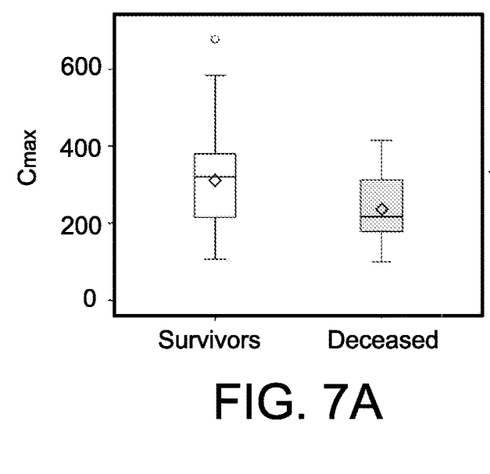
FIG. 7A shows a boxplot of non-limiting example portal vein flow parameter $c_{max}$ at 3-month mortality.
Figure 7B:
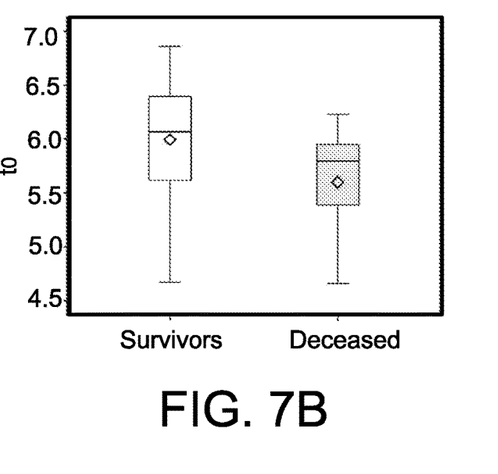
FIG. 7B shows a boxplot of non-limiting example portal vein flow parameter to at 3-month mortality.
Figure 7C:
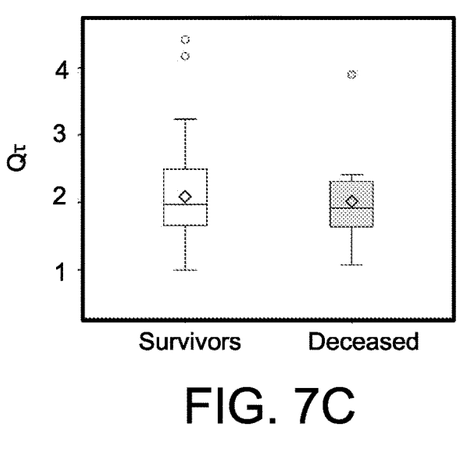
FIG. 7C shows a boxplot of non-limiting example portal vein flow parameter $Q_\tau$ at 3-month mortality.
Figure 7D:
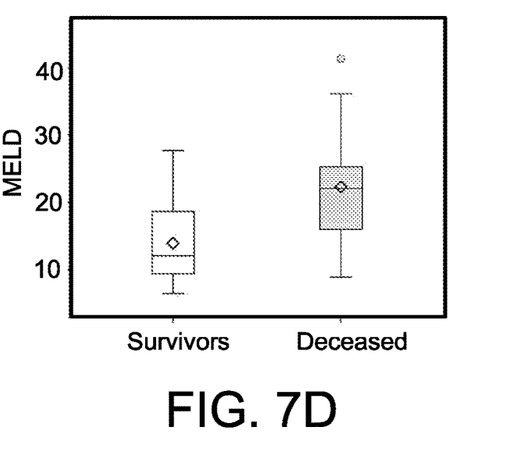
FIG. 7D shows a boxplot of non-limiting example MELD score at 3-month mortality.

Referring to FIGS. 7A-7D, flow parameters and model for end-stage liver disease (MELD) score of the non-limiting example vs. 3-month mortality rate are shown. FIG. 7A depicts flow parameter $c_{max}$, which corresponds to the maximum contrast intensity during the image series. FIG. 7B depicts flow parameter to, which is a factor to account for delay between the start of imaging and contrast increase. FIG. 7C depicts flow parameter $Q_\tau$, which is the portal vein flow time constant. FIG. 7D depicts the MELD score.

Figure 8:
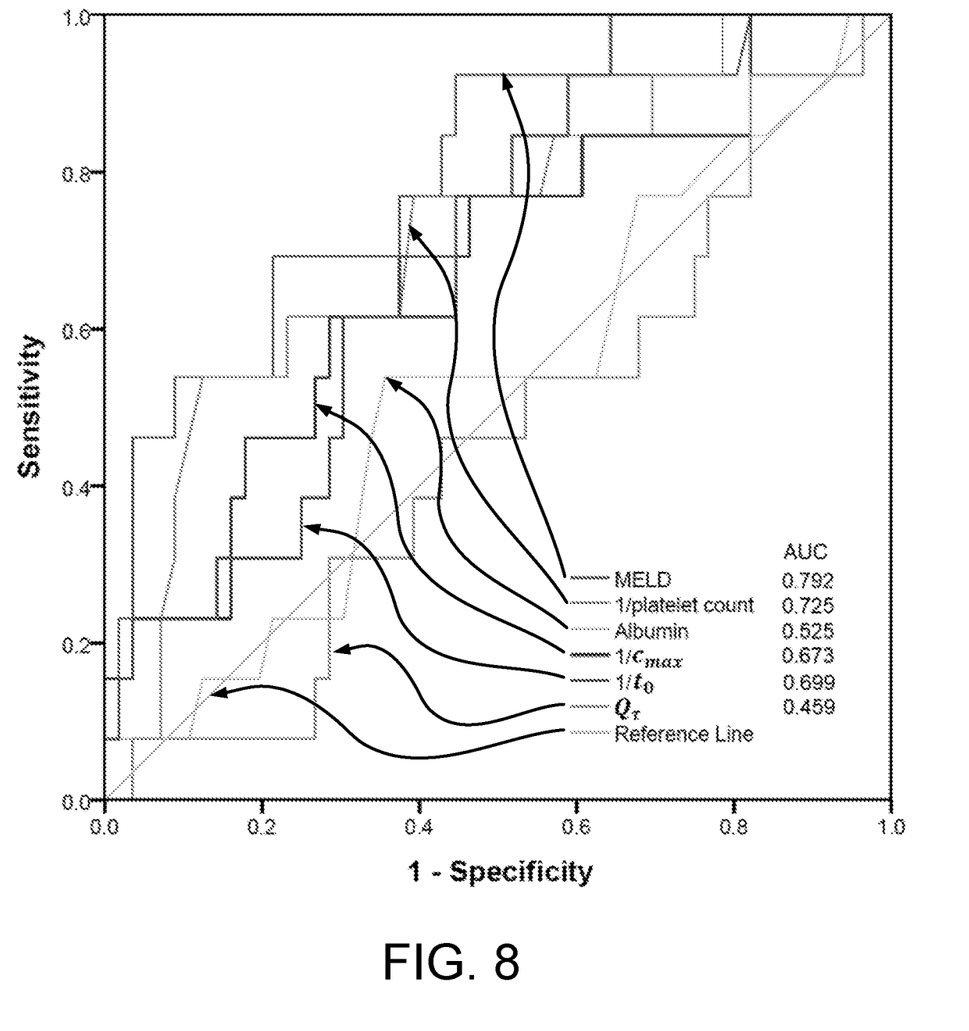
FIG. 8 shows non-limiting example ROC curves of flow parameters at 3-month mortality.

Referring to FIG. 8, ROC curves of flow parameters and model for end-stage liver disease (MELD) score of the non-limiting example vs. 3-month mortality rate are shown. Depicted flow parameters include the portal vein flow time constant $Q_\tau$, $c_{max}$, $t_0$, albumin and platelet count.

Although post-TIPS HE can usually be managed medically, for severe cases, a TIPS reduction is sometimes necessary. The portal vein flow time constant, $Q_\tau$, differed in cases that required TIPS reduction within a 12-month follow-up period. This is important because $Q_\tau$ reflects the rate of portal vein flow. Although post-TIPS HE was also significant for TIPS reduction, $Q_\tau$ was measured immediately after TIPS creation, whereas the HE diagnosis was made some time later. For this population sample, measures such as post-TIPS PSG and MELD score were relatively poor at discriminating cases that required TIPS angioplasty or reduction.

The present disclosure has described one or more preferred embodiments, and it should be appreciated that many equivalents, alternatives, variations, and modifications, aside from those expressly stated, are possible and within the scope of the invention.

The invention claimed is:

1. A method for assessing efficacy of placement of a vascular implant medical device that has been implanted in a subject, comprising:
accessing, with a computer system, image data acquired from a subject using a medical imaging system, wherein the image data include at least one image of the vascular implant device implanted within a vascular structure of the subject after the subject has received an injection of a contrast agent at a contrast injection site;
determining, from the image data, a region of interest (ROI) that includes the vascular structure and is downstream of the contrast injection site;
developing a contrast model from the image data;
using the contrast model, determining a flow time constant; and
using the flow time constant, assessing an efficacy of the vascular implant device implanted in the vascular structure.

2. The method of claim 1 wherein the ROI is downstream of the vascular implant device, and wherein the vascular implant device is downstream of the contrast injection site.

3. The method of claim 1 wherein the vascular implant device is a Transjugular intrahepatic portosystemic shunt (TIPS).

4. The method of claim 1 wherein the contrast model is:

$$c(t) = \begin{cases} 0 & t < t_a \\ c_{max} - e^{(t_0 - Q_\tau t)} & t_a \leq t < t_b \\ e^{(t_0 - Q_\tau t)} & t_b < t \end{cases}$$

where $Q_\tau$ represents a flow time constant, c represents contrast intensity; t represents time; $t_a$ and $t_b$ represent a bolus injection start and stop time, respectively, cmax represents a maximum contrast intensity, and $t_0$ represents a time delay factor to account for delay between a start of imaging and contrast increase.

5. The method of claim 4 further comprising assessing the efficacy of the vascular implant device relative to a portal vein, wherein $Q_\tau$ represents a portal vein flow time constant.

6. The method of claim 1 wherein the contrast model includes at least one of flow velocity or volumetric flow.

7. The method of claim 1 wherein the image data includes at least one of an x-ray imaging data, a computed tomography data, or a magnetic resonance imaging data.

8. The method of claim 1 further comprising estimating patient survival using the flow time constant.

9. The method of claim 1 wherein the contrast model includes a calibration value, wherein the calibration value is generated using at least one of ultrasound flow measurements or digital subtraction angiography (DSA) images.

10. A system for assessing efficacy of a vascular implant device that has been implanted in a particular position in a subject comprising:
a computer system configured to:
i) access image data acquired from a subject using a medical imaging system, wherein the image data includes at least one image of the vascular implant device implanted within the subject at a time after the subject has received an injection of a contrast agent at a contrast injection site;

ii) determine, from the image data, a region of interest (ROI) downstream of the contrast injection site;

iii) develop a contrast model from the image data;

iv) use the contrast model to calculate a flow time constant;

v) generate a report indicating an efficacy of the vascular implant device in the particular position in the subject using the flow time constant; and a display configured to display the report.

11. The system of claim 10 wherein the ROI is downstream of the vascular implant device, and wherein the vascular implant is downstream of the contrast injection site.

12. The system of claim 10 wherein the vascular implant device is a Transjugular intrahepatic portosystemic shunt (TIPS).

13. The system of claim 10 wherein the contrast model is:

$$c(t) = \begin{cases} 0 & t < t_a \\ c_{max} - e^{(t_0 - Q_\tau t)} & t_a \leq t < t_b \\ e^{(t_0 - Q_\tau t)} & t_b < t \end{cases}$$

where $Q_\tau$ represents a flow time constant, c represents contrast intensity; t represents time; $t_a$ and $t_b$ represent a bolus injection start and stop time, respectively, cmax represents a maximum contrast intensity, and $t_0$ represents a time delay factor to account for delay between a start of imaging and contrast increase.

14. The system of claim 13 wherein $Q_\tau$ represents a portal vein flow time constant.

15. The method of claim 13 wherein the contrast model includes at least one of flow velocity or volumetric flow.

16. The system of claim 10 wherein the image data includes at least one of an x-ray imaging data, a computed tomography imaging data, or a magnetic resonance imaging data.

17. The system of claim 10 wherein the computer system is further configured to estimate patient survival from the calculated flow time constant.

18. A method for supporting a clinical decision by characterizing flow within a subject's vasculature, comprising:

accessing, with a computer system, image data acquired from a subject using a medical imaging system, wherein the image data include at least one image of a vasculature of the subject at a time after the subject has received an injection of a contrast agent at a contrast injection site;

determining, from the image data, a region of interest (ROI) downstream of the contrast injection site;

extracting, using the image data, voxel intensity values for the ROI over time;

fitting the voxel intensity values to a contrast model;

calculating a flow time constant using the contrast model; and generating a report indicating efficacy of flow through the vasculature.

19. The method of claim 18 wherein the ROI is downstream of a vascular implant, and wherein the vascular implant is downstream of the contrast injection site.

20. The method of claim 18 wherein the contrast model is:

$$c(t) = \begin{cases} 0 & t < t_a \\ c_{max} - e^{(t_0 - Q_\tau t)} & t_a \leq t < t_b \\ e^{(t_0 - Q_\tau t)} & t_b < t \end{cases}$$

where $Q_\tau$ represents a flow time constant, c represents contrast intensity; t represents time; $t_a$ and $t_b$ represent a bolus injection start and stop time, respectively, cmax represents a maximum contrast intensity, and $t_0$ represents a time delay factor to account for delay between a start of imaging and contrast increase.

21. The method of claim 20, wherein $Q_\tau$ represents a portal vein flow time constant.

22. The method of claim 20 wherein the contrast model includes at least one of flow velocity or volumetric flow.

23. The method of claim 18 wherein the medical imaging system includes at least one of an x-ray imaging system, a computed tomography system, or a magnetic resonance imaging system.

24. The method of claim 18 wherein the report further indicates an estimate patient survival with the efficacy of flow through the vasculature.

* * * * *

UNITED STATES PATENT AND TRADEMARK OFFICE
CERTIFICATE OF CORRECTION

PATENT NO. : 11,769,252 B2
APPLICATION NO. : 17/263843
DATED : September 26, 2023
INVENTOR(S) : Aichi Chien Page 1 of 1

It is certified that error appears in the above-identified patent and that said Letters Patent is hereby corrected as shown below:

In the Specification

Column 3, Line 15, "to" should be --$t_0$--.

Column 9, Line 36, "to" should be --$t_0$--.

Signed and Sealed this
Twenty-first Day of November, 2023

Katherine Kelly Vidal
*Director of the United States Patent and Trademark Office*